United States Patent [19]

Kim

[11] Patent Number: 5,464,008
[45] Date of Patent: Nov. 7, 1995

[54] LAPAROSCOPE DEFOGGING

[76] Inventor: John H. Kim, 7411 Meandor Dr., Rockford, Ill. 61107

[21] Appl. No.: 227,388

[22] Filed: Apr. 14, 1994

[51] Int. Cl.$^6$ ...................................................... A61B 1/00
[52] U.S. Cl. ............................ 600/157; 600/158; 600/169; 600/183
[58] Field of Search ....................... 128/4, 6, 7; 606/192; 354/62

[56] References Cited

U.S. PATENT DOCUMENTS

| | | | |
|---|---|---|---|
| 5,167,220 | 12/1992 | Brown | 128/4 |
| 5,313,934 | 5/1994 | Wiita et al. | 128/4 |
| 5,349,941 | 9/1994 | Hori | 128/4 |

Primary Examiner—Linda C. M. Dvorak
Assistant Examiner—Beverly M. Flanagan
Attorney, Agent, or Firm—Robert M. Wolters

[57] ABSTRACT

A defogger for the objective lens of a laparoscope provides a channel in a longitudinal direction of the laparoscope. Gas from an insufflator is supplied to the channel exteriorly of a body being operated upon. A deflector is provided at or adjacent the opposite end of the gas flow channel to deflect insufflating gas across the objective lens for maintaining said objective lens clean within said body.

5 Claims, 3 Drawing Sheets

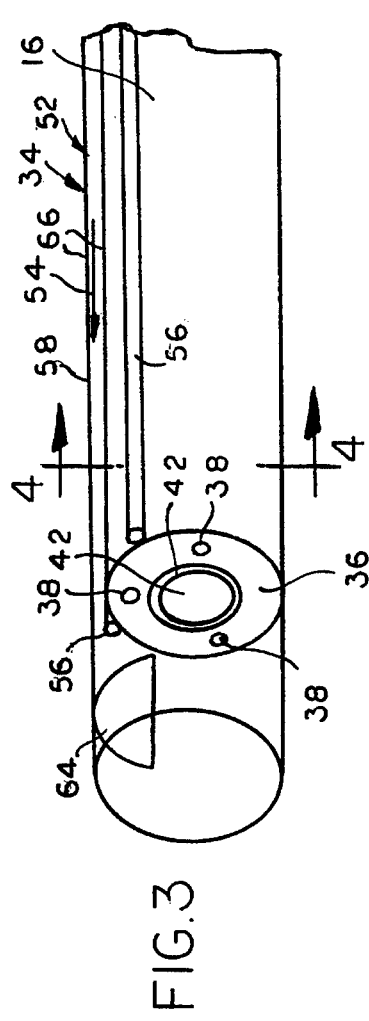
FIG.3
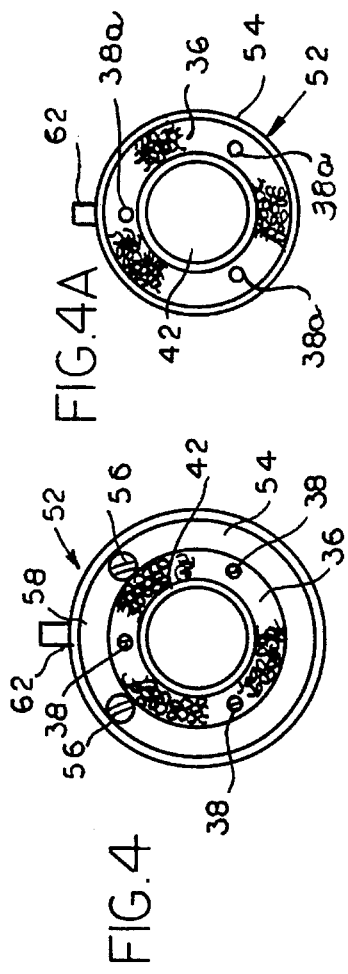
FIG.4A
FIG.4
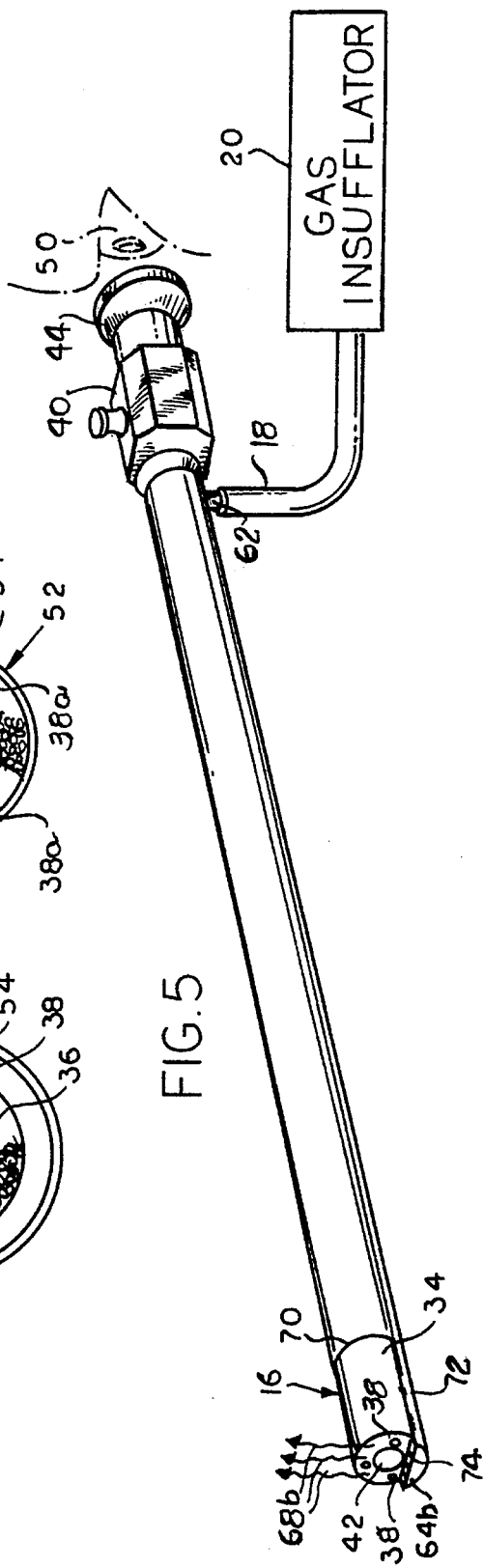
FIG.5

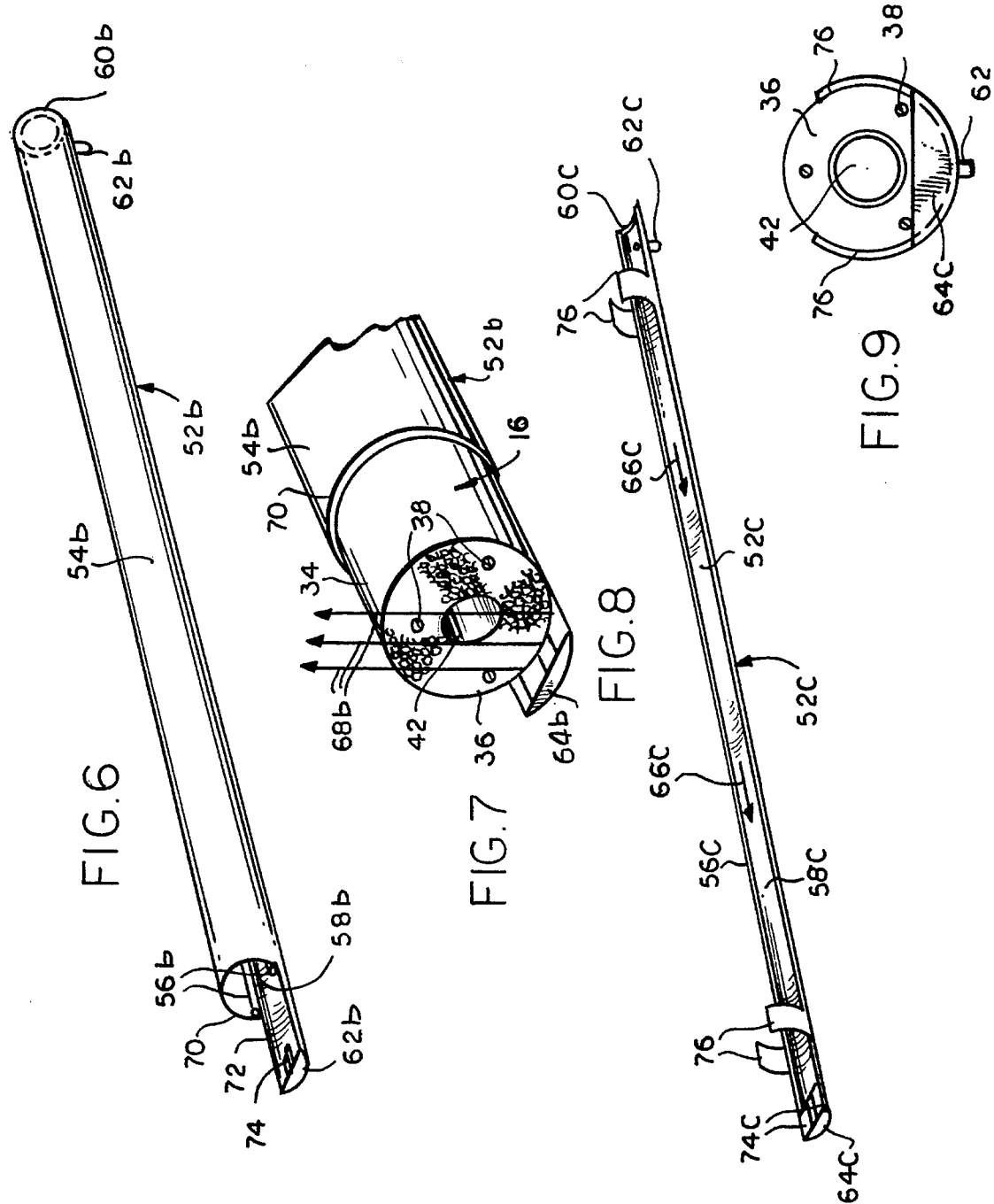

5,464,008

LAPAROSCOPE DEFOGGING

BACKGROUND OF THE INVENTION

Laparoscopic surgery at this time is well known. Instead of making large incisions in the body of the patient, many operations are carried out by use of a laparoscope. A laparoscope enters the abdominal cavity by way of a small hole through the skin and underlying tissues, generally through a cannula and trocar assembly. The trocar generally comprises a sharpened tubular instrument that simply punches through the skin and underlying tissue. The laparoscope has a fiber optic bundle for carrying light into the working area within the body, and optical means, generally comprising a series of lenses, for viewing the interior of the body. The viewing may be direct by the surgeon's eye at the exit end of the laparoscope, or it may have an electronic device at the exit end for sending signals to a monitor where the operative area can be viewed on an enlarged screen.

In order to provide adequate working and viewing room laparoscopic surgery generally is accomplished by insufflation of the interior of the body with a gas under pressure. Carbon dioxide is the preferred gas, since it is easily accommodated by the body, and is inexpensive. The gas may be supplied initially from pressurized tanks or bottles, and distributed to the laparoscope by an insufflator. After use, the gas passes from the body, and preferably is delivered to the hospital evacuation system.

The object lens of the laparoscope is obviously exposed to the interior of the body in which the surgery is being accomplished by a small diameter, remotely operable tool or device. Such a tool or device often includes a cauterization device which burns tissue and generates smoke, and may also sputter bits of tissue into the interior of the body. The tissue and smoke may for the object lens of the laparoscope, hindering visibility of the site of the operation. Another cause of fogging is condensation of moisture onto the cold lens surface.

Some progress has been made in the production of a laparoscope with means for removing image impeding material from the object lens. However, this does nothing for the thousands of laparoscopes now in the field. Such a laparoscope is disclosed in Auhll U.S. Pat. No. 5,207,213.

OBJECTS AND SHORT SUMMARY OF THE PRESENT INVENTION

It is an object of the present invention to provide an attachment for an existing laparoscope for defogging or cleansing the object lens of an existing laparoscope.

More particularly, it is an object of the present invention to provide such an attachment which does not materially increase the size of the hole into the body, and which uses insufflating gas for defogging or cleansing the object lens.

In achieving the foregoing and other objects, an attachment is provided for securement to the exterior of an existing laparoscope. Such attachment may be by way of an external cylinder enclosing the original laparoscope, or it may simply be a channel secured to the existing laparoscope, thus minimizing the size of the hole into the body. The attachment is provided with a channel through which the insufflating gas is passed into the body. The channel at the entering end is provided with a deflector for causing the gas to pass across the object lens, thereby defogging and otherwise cleaning the object lens without the necessity of any additional fluid being passed into the body over and above the insufflating gas which is otherwise necessary.

THE DRAWINGS

The invention will best be understood from the following description when taken in connection with the accompanying drawings wherein:

FIG. 3 is a perspective view on a further enlarged scale showing details of the object or distal end of the laparoscope with the present attachment thereon;

FIG. 4 is a cross section taken substantially along the line 4—4 in FIG. 3;

FIG. 4a is a cross section similar to FIG. 4 but showing a modification;

FIG. 5 is a view generally similar to FIG. 2, but showing a modification;

FIG. 6 is a view comprising a portion of FIG. 5, specifically the attachment of the present invention;

FIG. 7 is a perspective view of the object or distal end of the laparoscope attachment; and FIG. 8 is a view generally similar to FIG. 6, but showing a modification of the attachment; and FIG. 9 is a left end view of the attachment of FIG. as applied to the of FIG. 8, for example.

DETAILED DISCLOSURE OF THE ILLUSTRATED EMBODIMENTS

Figure 1:
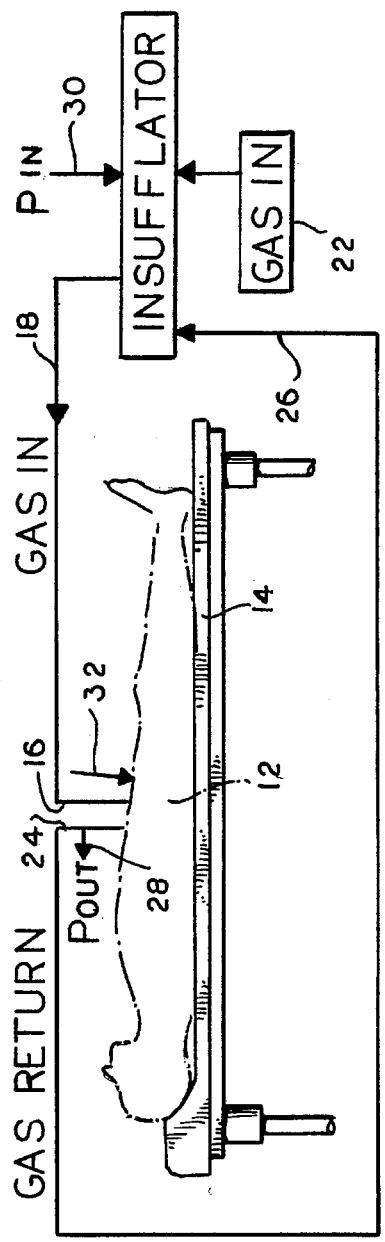
FIG. 1 is a somewhat schematic sketch illustrating application of the laparoscope and attachment, and insufflator gas flow to and from the body.

Attention first should be directed to FIG. 1 for a general understanding of the present invention. A patient 12 subject to a laparoscopic procedure is shown lying in supine position on an operating table 14. A laparoscope 16 is shown inserted into the abdomen of the patient through customary structures, including a well known cannula and trocar assembly (not shown), including the attachment to be disclosed later. Gas is supplied under pressure through suitable tubing 18 from an insufflator 20. A preferred gas is carbon dioxide, although argon and some other gases are satisfactory. Gas is provided from a source 22 to the insufflator. Such supply sources are well known, and generally comprise one or more tanks or bottles of compressed gas. The supply may be included as a part of the insufflator, and is shown separately for illustrative purposes.

Gas return from the patient is by way of a cannula and trocar assembly to a gas return line 24. This gas return line can be vented into the hospital ventilating system for discharge into the atmosphere, but preferably is returned to the insufflator at 26 for cleansing and reuse. A connection is made at 28 to the gas return line 24 to measure the internal pressure of the insufflating gas in the abdomen of the patient, and this output pressure is applied to a pressure end connection 30 to the insufflator to control the pressure and volume of gas supplied from the insufflator to the patient. A working tool 32 also is inserted through the skin and underlying tissue into the abdominal cavity for the respective treatment. Such tool generally comprises a remotely actuable surgical device, such, for example, as a cauterizing tool.

Figure 2:
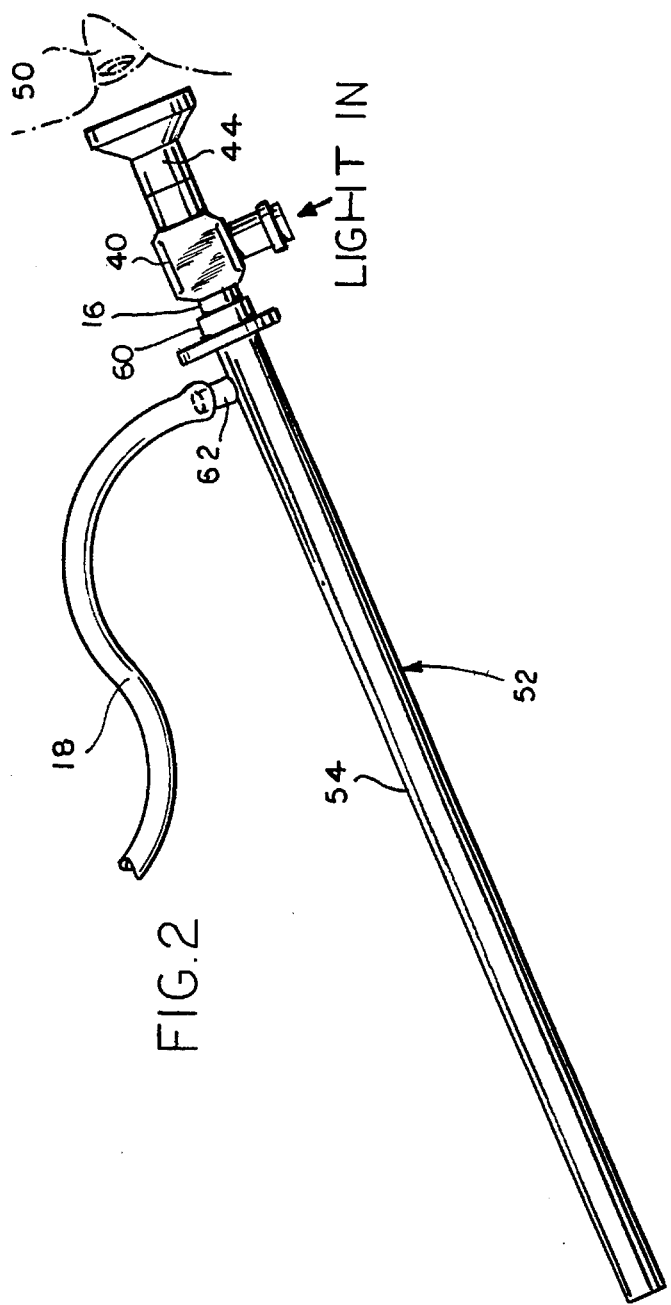
FIG. 2 is a side view of the insufflator with the present defogging attachment thereon.

Attention now should be directed to FIGS. 2–4 for an illustration of a first form or embodiment of the present invention. A conventional laparoscope 16 includes an elongated cylindrical housing 34 enclosing a fiber optical bundle 36. Elongated spacing rods 38 of solid construction extend through the optical fiber bundle. A connector 40 providing light to the optical fiber bundle is secured near the exit end of the laparoscope. The laparoscope further includes a means providing an optical path within the fiber optic bundle 36, and includes an object lens 42 and an exit eyepiece 44 through which the interior of the bodily cavity can be viewed by the human eye 50. Alternatively, the exit eyepiece 44 can be replaced by a suitable electronic pickup device for connection to a video monitor for showing the operating scene on an enlarged scale.

As is known, various bodily fluids and particles, and also smoke from cauterized tissue tend to fog the object lens 42. The defogger of the present invention is shown at 52, and comprises an elongated cylinder 54 extending from near the outer end of the laparoscope adjacent the light fitting 40 to somewhat beyond the entrance end of the laparoscope. Two elongated sealing members, which may be respectively cylindrical, are adhesively or otherwise suitably secured to the interior of the cylindrical housing 54 in circumferencially spaced relation in what conveniently is somewhat less than a 120° separation. A laparoscope and the defogger cylinder are axially telescoped with the sealing members 56 frictionally engaging the exterior of the sheath or housing 34 of the fiber optic bundle with the sealing members preferably sightly compressed against the sheath. This retains the defogger in position on the laparoscope. In the present embodiment of the defogger under discussion the sealing members 56 are generally along the top portion of the defogger and of the laparoscope. This provides an elongated conduit 58 defined by the sealing members 56, the fiber optic bundle sheath 34, and the housing 54 of the defogger. The upper portion of this conduit is sealed to the body of the laparoscope by an asymmetrical seal 60 adjacent the light connection 40.

Adjacent the seal, and downstream therefrom, is a lateral tubular gas connection 62 extending radially outwardly from the cylindrical housing or body 54. The hose or tubing 18 from the insufflator is received over this connection, and carbon dioxide, or other suitable insufflating gas from the insufflator is thus connected to the gas flow channel 58. The cover or housing 54 extends beyond the end of the laparoscope 16, and specifically beyond the objective lens 42. A deflector plate 64 is secured to and extends inwardly from the inner surface of the housing 54 at a position beyond the objective lens 42. Gas flows through the channel 58 as indicated by the arrow 66, and this gas flow is deflected radially inwardly as indicated at 68 across the face of the objective lens 42, thus preventing to a large extent deposition of any solid, liquid, or gaseous material on the face of the lens. Any such material is blown away by the gas passing across the surface of the lens, whereby the doctor has a clear view of the operative site at all times.

A modification of the invention is shown in FIG. 4a. Most of the parts are the same as heretofore shown and described, and similar numerals are utilized to identify similar parts. The cover 54 of the defogger is of lesser diameter, and substantially hugs the cover 34 of the fiber optic bundle. To provide for gas flow the reinforcing rods 38 have been converted to hollow tubes 38a, and gas flows through one or more of these tubes. The gas from the connection 62 passes directly to the uppermost tube 38a, and suitable plumbing connections can be utilized to connect gas flow through one or more of the lower tubes 38a. If gas is supplied to the lower tubes, then the deflector 64 can be replicated in respective locations, or the deflector may be a circular deflector of lesser radial dimension, whereby all of the gas is turned inwardly radially across the surface of the lens 42. As will be understood, one tube can supply gas, and a second tube can supply fluid through a valve to interrupt the flow. The fluid is deflected like the gas, and the fluid serves as an interrupted stream deflected to clean the lens surface in an interrupted manner.

A further modification of the invention is shown in FIGS. 5–7. The laparoscope 16 remains as originally disclosed, and similar numerals are used for the same parts. The defogger is somewhat modified, although most of the parts remain the same. Similar numerals are used with the addition of the suffix b. The important distinction is that the defogger is rotated 180°, and the entering end thereof mostly is terminated at 70 short of the end of the fiber optic bundle housing 34. However, the gas flow channel is extended beyond the end 70 by an extension 72 of the housing 54b. This extension 72 terminates beyond the objective lens 42, and the deflector 64b is provided at the end of the extension 72, thus deflecting gas up past the surface of the lens 42, indicated at 68b. Longitudinally extending baffles 74 strengthen the extension 72 and the deflector 62b, and help to control the direction of gas flow.

A further modification of the invention is shown in FIGS. 8 and 9 and may advantageously be used when it is desired to minimize cost, or to allow the defogger to be a one time use device. Parts are similar to those heretofore shown and described, and similar parts are identified by the use of similar numerals with the addition of the suffix c. In this embodiment the defogger does not comprise a complete cylinder, but rather a segment of a cylinder. Sealing members 56c are provided along the elemental edges of the cylindrical segment to press against the exterior surface of the laparoscope. Arcuate clips 76 extend from the elemental edges of the cylindrical segment to grip the laparoscope. Gas flow is the same as that previously described. One further embodiment is contemplated in which the clips 76 would be eliminated, and the seal members 56 would comprise adhesive sealing members to serve the dual purpose of adhering the defogger to the laparoscope, and sealing the defogger to the laparoscope to define the gas flow channel 58c.

The laparoscope defogger as disclosed herein is simple, effective and easy to produce. It can be made of material such that it can be autoclaved. This defogger allows continued use of the thousands of laparoscopes now in service worldwide, and does not require complete and expensive replacement thereof to effect defogging. A defogger in the present invention adds very little to the external dimensions of the laparoscope, and thus the added dimension has little effect on laparoscopic procedures. As is well known to those in the art the procedures are effected with part of the laparoscope within a bodily cavity and part of it outside of the body. Thus, it will readily be understood that part of the defogger is outside of the body, and that the gas tubing connector 62 has no effect on the transverse dimension of the laparoscope/defogger combination that must pass into the body.

The specific examples of the invention as herein shown and described are for illustrative purposes only. Various changes will no doubt occur to those skilled in the art, and will be understood as forming a part of the present invention insofar as they fall within the spirit and scope of the appended claims.

The invention is claimed as follows:

1. The combination comprising a laparoscope having a predetermined length and a predetermined transverse dimension with an objective end having an objective lens and further having a remote viewing end, and an insufflator supplying an insufflating gas under pressure, a laparoscope defogger comprising a body, means for securing said body snugly against said laparoscope exteriorly thereof, said laparoscope defogger having a gas flow channel extending along said laparoscope in the direction of said objective end lens, means for connecting said gas flow channel to said insufflator for receiving insufflating gas under pressure therefrom, and means on said defogger body for directing insufflating gas from said flow channel across the objective lens of said laparoscope for defogging said objective lens, and further including means spacing said body transversely of said laparoscope and providing said gas flow channel, a pair of elongated spacers spacing said body eccentrically about said laparoscope with said gas flow channel being defined by said body, said pair of spacers, and said laparoscope.

2. The combination comprising a laparoscope having a predetermined length and a predetermined transverse dimension with an objective end having an objective lens and further having a remote viewing end, and an insufflator supplying an insufflating gas under pressure, a laparoscope defogger comprising a body, means for securing said body snugly against said laparoscope exteriorly, thereof, said laparoscope defogger having a gas flow channel extending along said laparoscope in the direction of said objective end lens, means for connecting said gas flow channel to said insufflator for receiving insufflating gas under pressure therefrom, and means on said defogger body for directing insufflating gas from said flow channel across the objective lens of said laparoscope for defogging said objective lens, wherein said body is elongated in the direction of the length of said laparoscope, said body comprising a channel open along one side, and means securing said body alongside said laparoscope with said open side against said laparoscope, wherein said open side of said body has long edges, and sealing means along said edges for sealing said channel to said laparoscope.

3. The combination as set forth in claim 2 wherein said securing means and said sealing means comprise an adhesive material.

4. The combination comprising a laparoscope having a predetermined length and a predetermined transverse dimension with an objective end having an objective lens and further having a remote viewing end, and an insufflator supplying an insufflating gas under pressure, a laparoscope defogger comprising a body, means for securing said body snugly against said laparoscope exteriorly thereof, said laparoscope defogger having a gas flow channel extending along said laparoscope in the direction of said objective end lens, means for connecting said gas flow channel to said insufflator for receiving insufflating gas under pressure therefrom, and means on said defogger body for directing insufflating gas from said flow channel across the objective lens of said laparoscope for defogging said objective lens, wherein said gas flow channel is within said laparoscope.

5. The combination comprising a laparoscope having a predetermined length and a predetermined transverse dimension with an objective end having an objective lens and further having a remote viewing end, and an insufflator supplying an insufflating gas under pressure, a laparoscope defogger comprising a body, means for securing said body snugly against said laparoscope exteriorly thereof, said laparoscope defogger having a gas Flow channel extending along said laparoscope in the direction of said objective end lens, means for connecting said gas flow channel to said insufflator for receiving insufflating gas under pressure therefrom, and means on said defogger body for directing insufflating gas from said flow channel across the objective lens of said laparoscope for defogging said objective lens, wherein two channels are provided, one for gas and another for fluid which can be intermittently injected to clean the lens surface.

\* \* \* \* \*